United States Patent [19]

Barra

[11] Patent Number: 4,743,251
[45] Date of Patent: May 10, 1988

[54] VEIN PROTHESIS AND METHOD FOR PRODUCING SAME

[75] Inventor: Jean-Aubert Barra, Brest, France

[73] Assignees: Henry Bocquee; Jacques Gardette, both of Rungis, France; part interest to each

[21] Appl. No.: 708,425

[22] Filed: Mar. 5, 1985

Related U.S. Application Data

[63] Continuation-in-part of Ser. No. 613,394, May 22, 1984, abandoned.

[30] Foreign Application Priority Data

Dec. 8, 1983 [FR] France .................................. 83 19695

[51] Int. Cl.⁴ .............................................. A61F 2/06
[52] U.S. Cl. ...................................................... 623/1
[58] Field of Search ..................... 623/1, 11; 128/1 R, 128/334 R

[56] References Cited

U.S. PATENT DOCUMENTS

| Re. 31,618 | 7/1984 | Mano et al. | 623/1 |
|---|---|---|---|
| 3,425,418 | 2/1969 | Chvapil et al. | 623/1 |
| 3,974,526 | 8/1976 | Dardik et al. | 623/1 |
| 4,418,693 | 12/1983 | Laveen et al. | 623/1 |
| 4,469,101 | 9/1984 | Coleman et al. | 623/1 |
| 4,546,500 | 10/1985 | Bell | 623/1 |

Primary Examiner—Richard J. Apley
Assistant Examiner—David J. Isabella
Attorney, Agent, or Firm—Young & Thompson

[57] ABSTRACT

The prothesis is intended to be implanted in a human patient for forming an aorto-coronary by-pass or another by-pass on other arteries. The prosthesis comprises a normal, unaltered living vein which is taken from the patient himself/herself and which is surrounded by a multiperforated flexible sheath. The inside diameter of the sheath is so chosen that, after implantation, the outside diameter of the vein is maintained by the sheath at a value less than the maximum possible diameter of the vein and that the inside diameter of the vein is suitable for the diameter of the receiver artery.

7 Claims, 4 Drawing Sheets

VEIN PROTHESIS AND METHOD FOR PRODUCING SAME

This application is a continuation-in-part of my application Ser. No. 613,394 filed on May 22, 1984, now abandoned.

The present invention relates to a vein prothesis and the method for producing the prothesis.

The narrowing or complete obliteration of coronary arteries is at the present time treated by the surgical technique of aorto-coronary by-pass with a vein graft. A normal, unaltered vein is taken from the patient himself, maintained in the living state during handling and then transplanted to the heart level between the rising aorta on one hand, and the diseased coronary artery beyond the obstacle, on the other hand. This vein, which is employed as an arterial substitute, is termed an autotransplanted normal unaltered living vein graft. 6,000 patients have received in France per year this surgical treatment as an aorto-coronary by-pass graft.

The results of this surgical treatment deteriorate with time. In the long run, the evolution of autotransplanted living vein grafts is not satisfactory. After 10 years, about 50% of the grafts are obliterated. 25% of the grafts remaining permeable have atherome lesions. In all, 10 years after their implantation, only 25% of the grafts are considered to be sound. This lack of reliability over a long period is due to the graft disease.

This disorder is well known histologically. It starts with a subendothelial thickening: it is the subintimal hyperplasia. This initial lesion develops into the classical atheromatous plate with a stenosis of the graft. The development of the atheromatesis disease on grafts is unfortunately much more rapid than on the arteries.

The disease of the autotransplanted normal living vein graft results from the combination of multiple factors mentioned below:
1—individual factors;
2—genetic factors;
3—metabolic factors (lipides);
4—blood factors;
5—hemodynamic factors;
6—endothelial factors;
7—parietal physical factors.

Factors 1 and 2 cannot be treated with present therapeutics. Factors 3 and 4 may be well-controlled by medicinal therapeutics. Factors 5, 6 and 7 are not, at the present time, treated and the object of the invention is to reduce significantly the consequences of these three factors.

Further, it is known from U.S. Pat. No. 3,974,526 to produce vascular protheses from tanned or hardened veins obtained by the treatment of veins separated from umbilical cords which may include an external support formed by a mesh. This type of prothesis which does not employ a living vein does not permit the adaptation of the diameter of the graft to the receiver artery. Then Dardik Prothesis is not available under 4 mm in diameter. Moreover, it does not give satisfactory results in coronary surgery.

An object of the present invention is to provide a prothesis for implanting in a human patient. This composite prothesis is used as an aorto-coronary by-pass or a bypass on other arteries. This composite prothesis is formed by a normal unaltered living vein which is taken from the patient himself and is surrounded by a multiperforated flexible sheath, the inside diameter of the sheath being so chosen that, after implantation, the outside diameter of the vein is maintained by the sheath at a value less than the maximum possible normal vein diameter and such that the inside diameter of this vein is substantially or very close to the diameter of the receiver artery.

The sheath may be made from a material which is not resorbable by the receiving organism, such as synthetic fibers, in particular polyester fibres, the Dacron fibers, carbon fibres and Teflon. This sheath may also be made from a material which is slowly resorbable by the organism in which it is implanted.

This sheath is multiperforated or multiapertured. The evenly distributed perforations must be large enough to permit a neo-vascularisation of the outer walls of the implanted vein through these perforations. Moreover, the perforations must be small enough to avoid any hernia of the vein wall through the orifices of the perforations. In practice, perforations of 0.25 to 1 mm are suitable.

The sheath is cylindrical or slightly conical. The most simple example of this type of sheath is a cylindrical tubular mesh having fine mesh holes. But a perforated flexible tube may also be employed. It should be noted that the regularity of the internal surface of the mesh tube or sheath is important.

After implantation, the effect of the sheath is to maintain in a constrained condition the autotransplanted vein and therefore to maintain the outside diameter of the vein at such value that its inside diameter is substantially identical to or close to the receiver artery diameter which is suitable for the by-pass achieved.

Also, the diameter of the sheath is chosen in accordance with the thickness of the wall of the vein employed and of the caliber of the artery on which the vein is sutured.

In this respect, the hemodynamic factors must be considered.

One of the essential features of a living vein is its vasomotoricity, i.e. the possibility of reducing or increasing its caliber under the action of the muscles of the vein wall. The hydraulic pressure within a vein in a normal position usually does not exceed 20 mm of mercury. When this vein is used as a graft for an artery, it is subjected to the hydraulic conditions of an artery with a pressure of 150 mm of mercury. The parietal musculature of the graft cannot contain this pressure and the graft will increase in caliber up to the limit of extensibility. The parietal pressure is no longer supported by the muscular network of the vein wall but by the fibro-conjunctive network of the graft. It does not concern a partietal breakdown or aneuvrysmal pathologic process with expansion of the graft but a maximum caliber which the graft necessarily attains when it is subjected to the operating conditions of an artery, i.e. the arterial pressure. The maximum diameter, termed "standard definitive caliber", reached by the graft when it is subjected to the operating conditions of an artery as concerns pressure and flow, of course varies with the patient. However, it may be considered that this maximum diameter is usually between 3.5 and 4.5 mm when considering all the patients or at least 50% of the patients.

In respect of an aorto-coronary vein graft by-pass such a graft is branched to a coronary artery of 1.5 to 2 mm in diameter. The blood velocities in the graft are therefore between ¼ and 1/9th of those in the receiver artery.

The present invention makes it possible to impose on the vein a caliber which is in harmony with that of the receiver artery and prevent as it were the graft from developing to its maximum diameter. The present invention permits the obtainment of internal vein calibers of 2 to 3 mm and in particular 2 to 2.5 mm. The blood velocities in the graft are thus increased and are closed to the arterial circulatory velocities.

Consequently, by means of the present invention, it is possible to avoid the disturbances of the graft owing to an excessively low circulatory velocity.

Note also that each vein taken off has a certain number of collaterals. Each collateral is tied before severing. In the region of these collaterals, the diameter of the vein becomes enlarged. These enlargements correspondingly increase the maximum diameter of the graft. There are then observed circulatory slackening and turbulences with the result that the graft wall is harmed. The present invention permits the obtainment of a regular definitive caliber which is uniform throughout the length of the graft.

The endothelial factors must also be considered.

The graft, under arterial operating conditions, will develop toward its maximum diameter. Unfortunately, the endothelium, the unicellular layer which covers the inner surface of the vein wall, will not evenly match this maximum diameter. The maximum surface which may be covered by the vein endothelium is slightly less than that corresponding to this diameter. There are then produced ruptures in the continuity of the endothelial covering. The inner vein wall (basal membrane) will be bared here and there and will be in contact with the blood. The basal membranous components activate the blood platelets highly. The basal membrane is moreover permeable to the blood constituents, in particular the lipides, which will be diffused in the vein wall. These are important factors which intervene in the graft disease.

The present invention, in preventing the graft from developing towards its maximum diameter, guarantees a satisfactory endothelial covering of the inner vein wall. The lipidic infiltration and the platelet phenomena are significantly reduced. Thus, in the prothesis according to the invention, the sheath does not have merely for effect to consolidate the vein wall. The graft is sufficiently strong to resist the arterial pressure. The perivenous sheath has a constructive function which imposes a given diameter on the graft, this diameter being in harmony with that of the recipient artery.

Physical factors of parietal pressure also intervene in the graft disease. When the graft reaches its maximum diameter, the parietal muscular fibres are stretched to their maximum. The muscular fibres of the inner parietal layers will be stimulated by this stretching. As any muscle, they will become hypertrophied, will multiply, and thus precipitate in the subintimal hyperplasia. The sheath employed in the present invention reduces the stretching of the muscular fibres and should limit the hyperplasic reaction of the muscular fibres.

The sheath employed in the present invention affords moreover the following advantages or properties (a) The grafts have a tendency, if they are rather long, to bend at an acute angle. This slight technical defect may have dangerous consequences: acute obliteration of the graft followed by an myocardial infarct. The sheath gives a certain consistency to the graft and thus modifies its longitudinal and axial performance. The risks of folding are distinctly reduced, and the tolerance to excess of length of the graft increased.

(b) The sheath may be provided with a longitudinal reference mark which will avoid any axial torsion of the prothesis.

(c) Any traumastism, even minimum traumatism (dissecting tongs for example), involves and increases a risk of an endothelial damage with the baring of the basal membrane and its consequences already mentioned. The sheath permits a handling of the graft without touching the latter; it is merely sufficient to take hold of the sheath.

(d) The sheath permits the fixing of the graft to its environment. It is sufficient to fix the sheath to its environment.

The invention will be described hereinafter in more detail with reference to the accompanying drawings which show only embodiments of the invention.

Figure 1A:
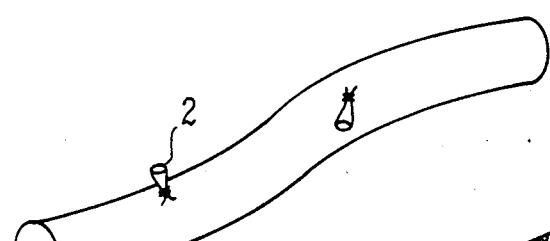
FIGS. 1A, 1B and 1C are diagrammatic perspective views of the various operating stages.

As shown in FIG. 1A, a vein 1 is taken from the patient to be operated. The collaterals 2 are ligatured. During the handling, the vein is maintained in condition under the usual conditions of preservation of organs. The vein is introduced in the sheath 3 which is formed by a cylindrical net or mesh having meshes which are oblique relative to its axis, the diameter of this sheath being chosen as indicated hereinbefore.

Figure 1B:
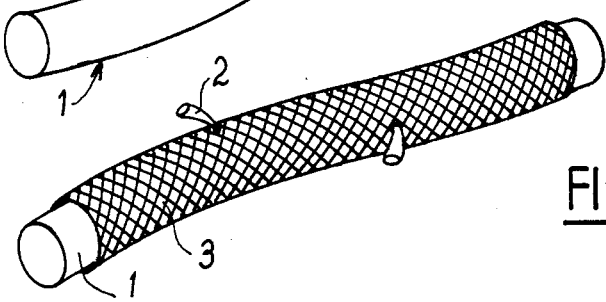

As shown in FIG. 1B, the vein collaterals 2 are drawn out of the mesh through the meshes of the latter. It may be necessary to enlarge the holes to permit the passage of the collaterals but the meshes must be made again with a thin thread. These collaterals 2 are thereafter secured to the sheath 3.

It is also possible to cut off the vein collaterals just at the level of the main vein and to close the remaining holes by superficial seams with a very thin thread which resorbs itself. The stitches of this seam do not perforate the endothelium. The seam may be in particular a "go and come" type surjet.

Figure 1C:
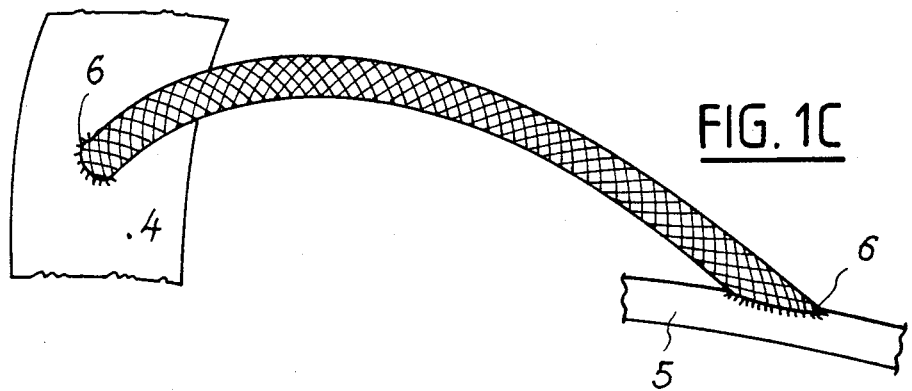

FIG. 1C shows an example of a by-pass between the aorta 4 of the patient and a coronary artery 5. The end of the sheath are joined either to the vascular anastomoses or to the immediately surrounding tissues by a few additional stiches 6 or in the course of the anastomoses.

For placing the sheath formed by a mesh around the vein, several devices may be used. Examples of four devices will be given hereinafter.

(1) USE OF AN INTERNAL SUPPORT (FIG. 2A)

Figure 2A:
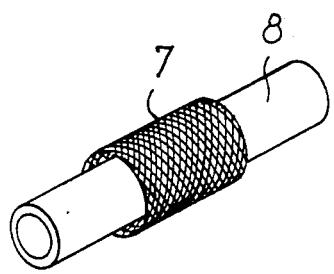
FIGS. 2A, 2B and 2C are perspective views of the various stages for placing the sheath around the vein.

As shown in FIG. 2A, the sheath 7 formed by a cylindrical mesh is placed on a tube 8 having a very thin wall.

Figure 2B:
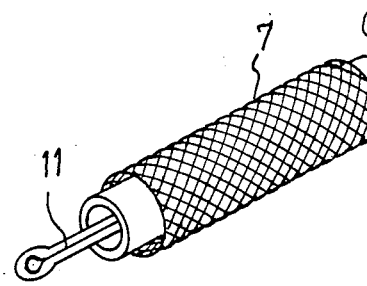

As shown in FIG. 2B, one of the ends 9 of the removed vein 10 is secured to a rod 11 which is inserted in the tube 8. The vein is thus drawn through the tube 8.

Figure 2C:
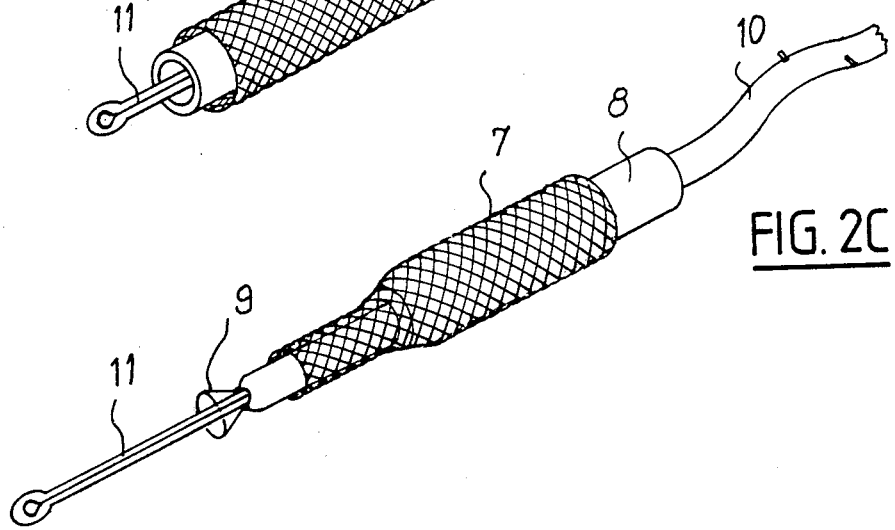

As shown in FIG. 2C, when the end 9 of the vein 10 issues from the tube 8, the mesh 7 is applied to the vein. The mesh 7 thus descends along the tube 8 onto the vein 10 at the rate at which the vein passes through the tube 8.

The tube may of course be replaced by an equivalent support, for example a support formed by three rods or two parallel strips.

The surgeon has available for each diameter a sheath on its support in a sterile condition and chooses the sheath in accordance with the criteria mentioned hereinbefore.

Figure 6A:
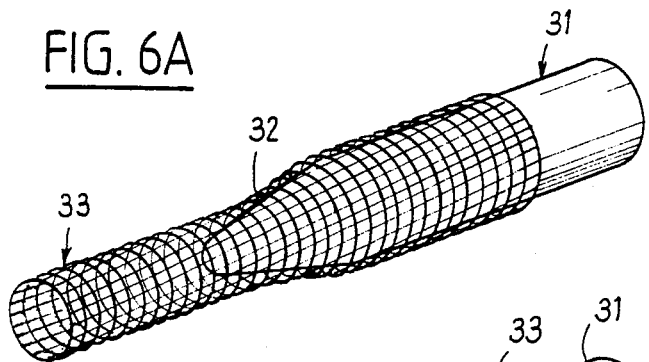
FIGS. 6A, 6B and 6C are perspective views of the various stages for placing a sheath around the vein by using another device.

However it has been found that the mesh becomes distorted when it stays on the internal support more than 24 hours. Thus, its caliber increases and its length decreases, affecting the mesh efficiency. Therefore it is preferable that the mesh is not set on its internal support by the manufacturer. The surgeon should carry out this operation just before the vein is taken, so that the mesh stay on the internal support will be very short. For this purpose it is advantageous to use an internal support tube 31 as shown in FIG. 6A. The support tube 31 is cylindrical and has a conical tip 32 which is then cut. The thickness of the tube 31 should be as thin as possible order to introduce veins of various calibers. This thickness is preferably not over 0.20 mm. Such a tube may be obtained from rigid plastic materials such as rigid-PVC, rigid polyurethane, polycarbonate or Teflon ®for example by injection moulding.

Figure 6B:
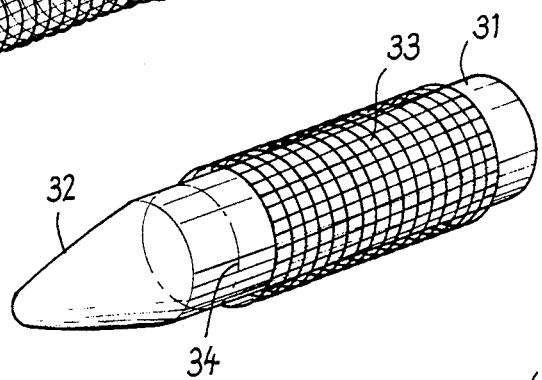

As shown in FIG. 6A, a mesh 33 is slipped by the surgeon (or his assistant), in the operating room, on the conical tip 32 of the tube 31 and thus easily placed on the tube as shown in FIG. 6B.

Afterwards the surgeon removes the blind conical tip 32 by cutting at 34 the tube 31 near the conical tip by using scissors. Thus he obtains a mesh 33 place on a tube open at both ends.

Figure 6C:
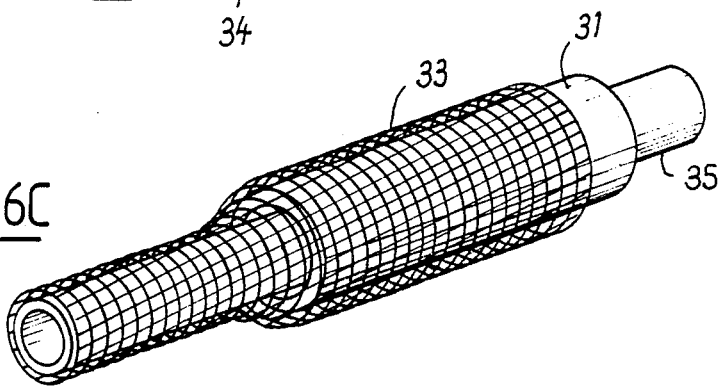

As shown in FIG. 6C a vein 35 is then drawn through the tube 31, as previously described.

Figure 7:
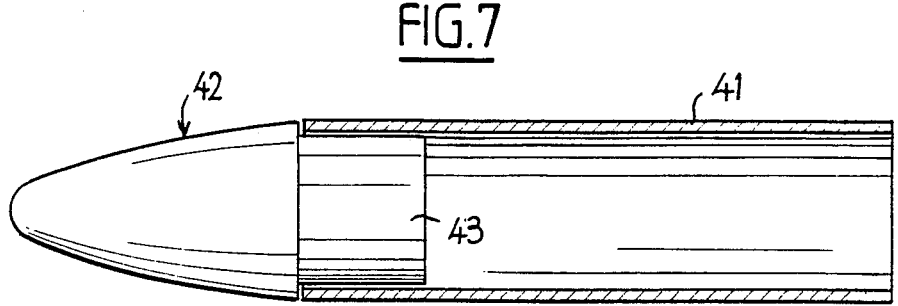
FIG. 7 is a section of a modification of a device for placing the sheath on the vein.

FIG. 7 shows a modification of the tube shown in FIG. 6A. The tube 41 is cylindrical and open at both ends. It has a length of about 150 mm, a thickness of about 0.2 mm. At one end is placed a removable tip 42 having an external conical shape, this tip 42 being secured to the tube 41 by a cylindrical part 43 which is inserted into the end of the tube 41.

(2) USE OF A SUPPORT INCORPORATED IN THE SHEATH (a) The perivascular sheath may be impregnated with a non-toxic, biodegradable, non-irritating substance which hardens upon drying. This substance must be soluble in a solvent satisfying the same criteria as the substance. The simplest example of a solvent is the physiological saline solution. Among the possible products may be mentioned glucose, saccharose, starch, macro-molecules, etc . . . The contact of the solvent or of the impregnation product must not alter the endothelium of the vein. The sheath impregnated with its stiffening product is dried in the shape of a tube so as to permit the insertion of the vein in the tubular sheath thus formed and allow it to slide along the longitudinal axis of the sheath. Several calibers of sheath are available to the surgeon. The stiffened sheath must be sterile and preserved under sterile conditions.

When the vein has been positioned in the tube formed by the stiffened sheath, the assembly is plunged in the solvent which, after a plurality of rinsings, dissolves practically the whole of the stiffening product. The assembly of the sheath and vein than becomes flexible. The collaterals of the vein are then drawn out of the sheath through the meshes, as in the previous case.

(b) The support may be an integral part of the sheath. It concerns a device which maintains the sheath open and imparts thereto the appearance of a flexible tube. It may concern a series of rings or a spiral adhered to the exterior of the sheath or incorporated in the meshes and imparts the tubular shape to the sheath. This device, which permits the introduction of the vein in the sheath is of a material which is resorbed or not resorbed by the organism.

Figure 3:
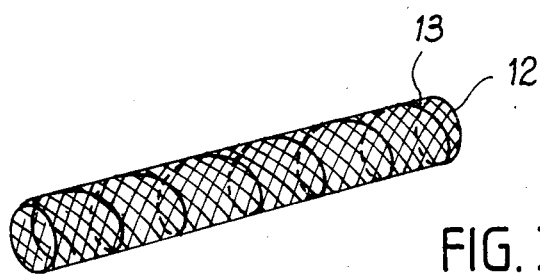
FIG. 3 is a perspective view of a modification of a sheath.

FIG. 3 shows an embodiment of a sheath 12 formed by a longitudinal net or mesh including a supporting spiral 13.

(3) EXTERNAL SUPPORT FOR THE SHEATH

In this case, the sheath is inside the support which may be a tube, three rods, two strips, a series of rings or a spiral. The sheath is secured to its support by a device which may be eliminated (for example overstitching). The sheath therefore remains open and the vein can be axially and longitudinally inserted therein.

Figure 4:
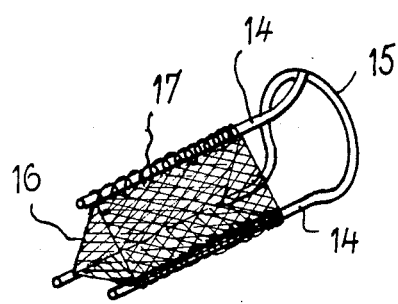
FIG. 4 is a perspective view of a modification of a device for placing the sheath in position.

An embodiment of such a device is shown in FIG. 4. This device comprises three spacer rods 4 which are rigid at one end with a loop 15. A net or mesh 16 is held taut between the rods 14 by means of fixing threads 17 surrounding the rods 14, which threads are eliminated after the vein has been inserted.

(4) INTERNAL AND EXTERNAL SUPPORTS (FIG. 5)

Figure 5:
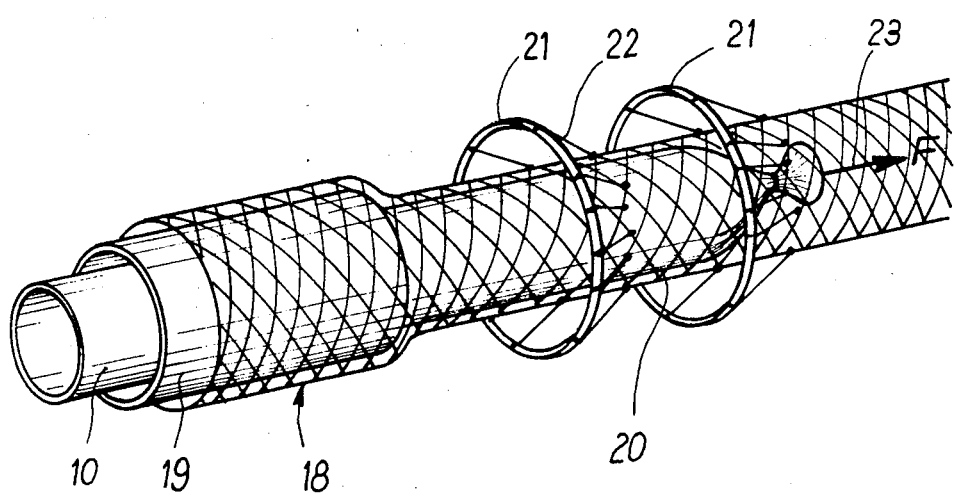
FIG. 5 is a perspective view of another device.

As shown in FIG. 5 a first part 18 of the mesh is supported by an internal support tube 19 having a thin wall. A second part 20 is supported by two external supports 21. Each external support 21 comprises a ring which is connected to the second part 20 of the mesh by threads 22. The diameter of the second part 20 is the final diameter of the graft. Secured to the end of the vein 10 is a thread 23 which is inserted in the tube 19 and then in the second part 20 of the mesh. This thread 23 Is used for pulling the vein (in the direction of the arrow F). When the vein 10 is pulled through the second part 20 of the mesh, the diameter of this part tends to diminish, thus blocking the vein. By pulling the rings 21 in the opposite direction, the diameter of the part 20 is enlarged and the vein may be pulled again. When there is a new blocking of the vein, the rings 21 are again pulled in the opposite direction. In this way, the whole of the vein is inserted into the mesh step by step.

After removal of the rings 21, the threads 22 and the first part 19, a composite graft is obtained. This graft has a diameter which is well defined.

Examples of carrying out the invention in the animal and in man will now be given.

EXAMPLE 1

The animal experiment was carried out on four sheep.

1. 10 cm of left jugular vein was taken and used as an autotransplanted living vein graft. The vein is divided into two segments having a length of 5 cm.

2. Left side:

There is affected a resection of 5 cm of primitive carotid artery (diameter 6 mm). This artery segment is replaced by 5 cm of a vein removed at the start of the surgical operation. This by-pass corresponds to the prior art.

The anastomoses are end-to-end.

3. Right side:

A resection of 5 cm of the primitive carotid artery (diameter 6 mm) is effected. This artery segment is replaced by the mounting of a vein disposed in a perivascular sheath having a diameter of 7 mm and a mesh hole size of 1 mm according to the invention.

The anastomoses are end-to-end and the sheath is secured by a few surface stitches to the primitive carotid artery at the ends of the vein.

4. Immediate results:

After putting under pressure:

on the left, the caliber of the vein graft is 14 mm, on the right, the vein in its sheath has a caliber of 7 mm.

5. Histological results at the fourth month following the operation.

The walls of the sheathed graft according to the invention are thinner than the walls of the unsheathed. The left graft wall thickness ranges from 4/3 to 3 times the right graft wall thickness (surrounded vein).

On only one sample, the unsheathed vein is the centre of sub-intimal macrophage infiltration containing lipide deposits (first stage of the atheromatous degeneration). This phenomenon is not observed in the sheathed vein according to the invention.

EXAMPLE 2

In a new experiment on sheep, two groups of sheep were used. The group 1 (control group) included 6 jugular grafts according to the prior art. The group 2 included 8 jugular grafts surrounded by a mesh in accordance with the present invention. In group 1 the graft diameter was 15 mm±1 mm and in group 2 the graft diameter was 7 mm±0.5 mm. The veinous wall thickness in group 1 was twice greater than in group 2.

In group 1 the veinous wall is fibrotic with many fibroblasts. In contrast in group 2 the veinous wall is a regular layer of normal smooth myocytes. External elastic layer is broken in group 1 but not in group 2. The election scanning micrographs shown in group 1 a deteriorated endothelium (irregular cells separated one from the other, fibrin deposit, stripping of the basal membrane). In contrast in group 2 the endothelium is normal.

EXAMPLE 3

Right humero-radial bridging with a saphenous vein graft sheathed in a net or mesh having a diameter of 3.5 mm and a mesh size of 1 mm in a patient aged 25 years having a post-traumatic obliteration of the right cubito-radial arteries.

1. The internal saphenous vein of the right leg is taken and the collaterals are tied. A pressure of 150 mm of mercury is applied on a 2 cm long fragment for ¼ hour. The spontaneous final caliber of the sample reaches a diameter of 4.5 mm. The uninflated normal vein is inserted in the perivascular sheath having a diameter of 3.5 mm, as explained before. The effective diameter of the orifice of the vein thus assembled is 2.8 mm.

2. The humeral artery at the fold of the elbow and the radial artery at the wrist are dissected. The vein in its sheath is implanted between the lower humeral (caliber 5 mm) and the terminal right radial artery (caliber 2 mm). The anastomoses are lateral-end above and end-lateral below. The sheath is secured to the anastomoses by a few additional separate stitches.

3. Arteriographic result 3 months after the surgical operation.

The sheathed vein graft is clearly seen in the arteriography, its caliber is uniform: 2.5 mm in diameter, the inner walls of the graft appear to be smooth, regular and without hooking of the contrast product on the endothelium.

EXAMPLE 4

4 patients were given a saphenous graft surrounded by mesh system as on aorto-coronary by-pass. Previous saphenous diameters were 5 mm, 4.5, 3.5 and 3.5 mm. The meshes resulted in a graft diameter of 4, 3, 3.5, 2.8 and 2.5 mm respectively. Angiographic checking after 2 months show grafts of 4, 3 and 2.5 and 2.2 mm diameters, with a very regular caliber.

What is claimed is:

1. A method for producing a prothesis for implanting in a human patient so as to form a bypass or arteries such as aorto-coronary bypass, said prothesis comprising a living vein which is taken from the patient and a multi-perforated flexible sheath surrounding the vein, said method comprising taking a vein from the patient, surrounding said vein with a multi-perforated flexible sheath, said sheath having an inside diameter which is so chosen that, after implantation, said vein is constrained by said sheath so that its outside diameter is maintained by said sheath at a value less than the maximum possible diameter of said vein and that its inside diameter is substantially or very close to the receiver artery diameter.

2. A method according to claim 1, wherein said sheath is a mesh.

3. A method according to claim 2, comprising slipping, just before the vein is taken, the mesh on a tube having a thin wall, pulling the vein through the tube and applying the mesh on the vein when the vein has passed through the tube.

4. A method according to claim 3, comprising slipping the mesh on a tube having a conical tip and then removing the tip by cutting.

5. A method according to claim 3, comprising slipping the mesh on a tube having a removable conical tip.

6. A method for forming a bypass with a vein on a human patient who has an artery which has a narrowing or an obliteration, said method comprising taking an unaltered vein from the patient, surrounding said vein with a multi-perforated flexible sheath, said sheath having an inside diameter which is so chosen than, after implantation, the vein is constrained by said sheath so that its outside diameter is maintained by said sheath at a value less than the maximum possible diameter of said vein and that its inside diameter is substantially or close to the diameter of the receiver artery, and proceeding to the forming of said bypass with said vein surrounded by said sheath.

7. A method according to claim 7, wherein said bypass is an aorto-coronary bypass.

* * * * *